US012649030B2

(12) United States Patent
Mosebach et al.

(10) Patent No.: US 12,649,030 B2
(45) Date of Patent: Jun. 9, 2026

(54) SYRINGE SUPPORT AND AUTOINJECTOR

(71) Applicant: Sanofi-Aventis Deutschland GMBH,
Frankfurt am Main (DE)

(72) Inventors: Carsten Mosebach, Frankfurt am Main
(DE); Thomas Mark Kemp, Ashwell
(GB)

(73) Assignee: Sanofi-Aventis Deutschland GMBH,
Frankfurt am Main (DE)

( * ) Notice: Subject to any disclaimer, the term of this
patent is extended or adjusted under 35
U.S.C. 154(b) by 806 days.

(21) Appl. No.: 17/308,831

(22) Filed: May 5, 2021

(65) Prior Publication Data

US 2021/0252223 A1 Aug. 19, 2021

Related U.S. Application Data

(63) Continuation of application No. 15/579,052, filed as
application No. PCT/EP2016/062447 on Jun. 2, 2016,
now Pat. No. 11,027,068.

(30) Foreign Application Priority Data

Jun. 3, 2015 (EP) .................................... 15170579

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157*
(2013.01); *A61M 2005/2013* (2013.01); *A61M
5/3204* (2013.01); *A61M 2205/581* (2013.01)

(58) Field of Classification Search
CPC ........ A61M 5/2033; A61M 2005/2006; A61M
2005/2026; A61M 5/3243; A61M
2005/2013; A61M 2005/2418; A61M
2005/2437; A61M 2005/244; A61M
2005/2477
See application file for complete search history.

(56) References Cited

U.S. PATENT DOCUMENTS 3,144,178 A 8/1964 Sarnoff
5,000,744 A 3/1991 Hoffman et al.
(Continued)

FOREIGN PATENT DOCUMENTS

CN 103167888 6/2013
CN 104394912 3/2015
(Continued)

OTHER PUBLICATIONS

Third Party Observations in European Patent Application No.
16726328.4, dated Aug. 23, 2018, 24 pages.
(Continued)

*Primary Examiner* — Emily L Schmidt
*Assistant Examiner* — Samuel J Marrison
(74) *Attorney, Agent, or Firm* — Fish & Richardson P.C.

(57) ABSTRACT

The disclosure relates to a syringe support for supporting an
axial position of a syringe relative to a housing of an
autoinjector. The syringe support includes a supporting
beam arranged on the syringe support and biased radially
inwards. The supporting beam is adapted to axially bias the
syringe in a distal direction within the housing. The disclo-
sure further relates to an autoinjector.

27 Claims, 7 Drawing Sheets

(56)      References Cited

U.S. PATENT DOCUMENTS

| | | | |
|---|---|---|---|
| 5,078,698 A | 1/1992 | Stiehl et al. | |
| 5,320,609 A | 6/1994 | Haber et al. | |
| 5,372,590 A | 12/1994 | Haber et al. | |
| 5,462,740 A | 10/1995 | Evenstad et al. | |
| 5,681,291 A * | 10/1997 | Galli .................... | A61M 5/2033 |
| | | | 604/162 |
| 6,186,980 B1 | 2/2001 | Brunel | |
| 6,210,369 B1 | 4/2001 | Wilmot et al. | |
| 7,118,552 B2 | 10/2006 | Shaw et al. | |
| 8,647,299 B2 | 2/2014 | Stamp | |
| 9,011,389 B2 | 4/2015 | Peruzzo et al. | |
| 2001/0005781 A1 | 6/2001 | Bergens et al. | |
| 2003/0105430 A1 | 6/2003 | Lavi et al. | |
| 2004/0127857 A1 | 7/2004 | Shemesh et al. | |
| 2005/0101917 A1* | 5/2005 | Doyle ................... | A61M 5/326 |
| | | | 604/187 |
| 2005/0115507 A1 | 6/2005 | Halachmi et al. | |
| 2007/0111175 A1* | 5/2007 | Raven ................. | G09B 23/285 |
| | | | 434/262 |
| 2007/0129686 A1* | 6/2007 | Daily .................... | A61M 5/326 |
| | | | 604/137 |
| 2007/0173770 A1 | 7/2007 | Stamp | |
| 2011/0178501 A1* | 7/2011 | Cleathero ............. | A61M 5/326 |
| | | | 604/506 |
| 2013/0006192 A1* | 1/2013 | Teucher .............. | A61M 5/2466 |
| | | | 604/201 |
| 2014/0066863 A1 | 3/2014 | Nzike | |
| 2014/0330216 A1 | 11/2014 | Weaver et al. | |
| 2015/0119809 A1 | 4/2015 | Loof | |
| 2015/0258278 A1* | 9/2015 | McLoughlin ........... | A61M 5/20 |
| | | | 604/154 |
| 2017/0348489 A1 | 12/2017 | Hirschel et al. | |

FOREIGN PATENT DOCUMENTS

| | | | | |
|---|---|---|---|---|
| EP | 2722066 | 4/2014 | | |
| JP | 2003-511105 | 3/2003 | | |
| JP | 2009-523587 | 6/2009 | | |
| JP | 2013-533062 | 8/2013 | | |
| JP | 2014-502891 | 2/2014 | | |
| WO | WO 1999/022792 | 5/1999 | | |
| WO | WO-2005070481 A1 * | 8/2005 | ........... | A61M 5/178 |
| WO | WO 2007/083115 | 7/2007 | | |
| WO | WO 2010/043533 | 4/2010 | | |
| WO | WO 2011/123024 A1 | 10/2011 | | |
| WO | WO 2012/017035 | 2/2012 | | |
| WO | WO 2012/064258 | 5/2012 | | |
| WO | WO 2012/064259 | 5/2012 | | |
| WO | WO 2012/089620 | 7/2012 | | |
| WO | WO-2013032389 A1 * | 3/2013 | ......... | A61M 5/2033 |
| WO | WO 2013/156350 | 10/2013 | | |
| WO | WO 2014/174519 | 10/2014 | | |
| WO | WO-2015121080 A1 * | 8/2015 | ............. | A61M 5/20 |
| WO | WO 2016/134491 | 9/2016 | | |
| WO | WO 2016/193340 A1 | 12/2016 | | |
| WO | WO 2016/193341 A1 | 12/2016 | | |

OTHER PUBLICATIONS

International Preliminary Report on Patentability in International Appln. No. PCT/EP2016/062447, dated Dec. 5, 2017, 6 pages.
International Search Report and Written Opinion in international Appln. No. PCT/EP2016/062447, dated Aug. 18, 2016, 9 pages.
Third Party Observations in European Patent Application No. 16726328.4, dated Jan. 19, 2022, 10 pages.

\* cited by examiner

SYRINGE SUPPORT AND AUTOINJECTOR

CROSS REFERENCE TO RELATED APPLICATIONS

The present application is a continuation of U.S. patent application Ser. No. 15/579,052, filed Dec. 1, 2017, which is the national stage entry of International Patent Application No. PCT/EP2016/062447, filed on Jun. 2, 2016, and claims priority to Application No. EP 15170579.5, filed in on Jun. 3, 2015, the disclosures of which are expressly incorporated herein in entirety by reference thereto.

TECHNICAL FIELD

The disclosure relates to a syringe support and to an autoinjector.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by a plunger which has to be continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). And, aligning the injection device, administering the injection, and keeping the injection device still during the injection may require dexterity which some patients may not have.

Autoinjector devices may be single-use or reusable devices and aim to make self-injection easier for patients. A conventional autoinjector may completely or partially replace activities involved in parenteral drug delivery from a manual device. Typically, such activities include removal of a protective syringe cap, insertion of the needle, providing the force for administering the injection and possibly removal and shielding of the used needle.

There remains a need for a syringe support within the autoinjector and an improved autoinjector comprising such a syringe support so that the autoinjector and its components, in particular a syringe, are securely arranged within a housing.

SUMMARY

In some aspects, a syringe support and an improved autoinjector with such a syringe support is provided.

Exemplary embodiments of the invention are given in the dependent claims.

One aspect of the present disclosure relates to a syringe support for supporting an axial position of a syringe relative to a housing of an autoinjector, wherein the syringe support comprises a supporting beam arranged on the syringe support and biased radially inwards, wherein the supporting beam is adapted to axially bias the syringe in a distal direction within the housing.

The syringe support provides a secure arrangement of the syringe within the housing. In particular, the syringe support allows tolerance compensation. For example, the syringe support allows that syringes with different lengths due to manufacturing tolerances may be arranged within the same housing. Furthermore, the syringe support prevents rattle of the syringe in the housing and at least reduces and prevents axial movement of the syringe which otherwise could cause the protective needle shield to be displaced relative to the syringe, potentially impacting sterility.

In an exemplary embodiment, the supporting beam is adapted to accommodate a variable length of the syringe within the housing in the distal direction. In other words, the supporting beam provides a secure arrangement by compensating different syringe lengths. In particular, the supporting beam is adapted to compensate the length of the syringe of maximum 5%, in particular 3%. For example, the syringe support accommodates +/−1.5 mm syringe length for a syringe of 50 mm in length.

Additionally, for syringes with a smaller length, the supporting beam may damp a shock of an impact force due to falling so that the syringe is less prone to damages. For instance, due to impact forces on an end of the autoinjector, the syringe moves rearwards, a portion of the supporting beam deflects and further stresses radially outwards so that the rearward movement of the syringe can be absorbed, in particular damped and restricted.

In an exemplary embodiment, the supporting beam is located distally on the syringe support. Thereby, the distal supporting beam retains the syringe in position. Furthermore, more than one supporting beams may be arranged around the circumference of the syringe flange, thus the syringe is reliably held in position.

In an exemplary embodiment, the supporting beam is formed as a flexure beam. In particular, the supporting beam is formed as a radially inward half-arc or arc enabling the supporting beam to be maintained in a relaxed position and to form a stop for the syringe for compensating different syringe length. Furthermore, the supporting beam may be stressed during assembling of the syringe due to different length of the syringe to avoid or at least minimize risk of damages. For instance, during assembling, the syringe is carried and holds by a syringe carrier at its distal end wherein the proximal end, namely the flange, of the syringe projects the proximal end of the syringe carrier so that a portion of the supporting beam, engaging the flange, deflects and further stresses radially outwards so that the length of the syringe can be compensated.

Furthermore, the supporting beam may be formed from resilient material. In particular, the resilient supporting beam could be in the form of an arc of resilient material, wherein at least one end of the arc is attached to the housing and an outer free end of the arc is in juxtaposition with the flange of the syringe.

In a further embodiment, one end of the supporting beam is attached to the syringe support and an opposite end is a free end. In particular, the supporting beam is integrated into the syringe support wherein the supporting beam extends radially inwards from a recess or aperture in the syringe support so that the supporting beam deflects radially outwards into the recess or aperture when the syringe is assembled or moves rearwards. In an alternative embodiment, both ends of the supporting beam may be attached to the syringe support, e.g. to opposite ends of the aperture in the syringe support. Such a supporting beam may be part of the syringe support and may be integrated into the aperture as a bent or arc. In particular, the supporting beam may be integrally moulded with the syringe support for ease of manufacture.

Furthermore, the syringe support may comprise a number of apertures adapted to form a corresponding number of supporting beams that interact with the flange of the syringe for providing a length compensation or a damping and a restricting of an axial movement of smaller syringes rearwards when the syringe is assembled and in place within the housing. Furthermore, the supporting beams may be arranged around the circumference of the syringe flange, thus the syringe is reliably held in position.

In a further embodiment, at least two supporting beams are arranged on the syringe support. The at least two supporting beams are arranged opposed to each other. More than two supporting beams may be provided and may be symmetrically arranged on the syringe support. Further, the at least two supporting beams are formed as flexure beams, e.g. as a radially inward bent, for instance a half-arc or arc.

In an exemplary embodiment, the at least two supporting beams have different free ends wherein one of the free ends is bent and the other free end is straight. In an assembled state of the autoinjector, the different free ends of the supporting beams laterally extend beyond the flange of the syringe. Hence, the flange of the syringe abuts the different free ends. The different free ends are adapted to provide a secure axial support and positioning of the syringe relative to the housing in the rearward direction. Thus, a risk of breakage is reduced. This increases the range of geometrical syringe lengths that can be accommodated.

According to another aspect of the disclosure, an autoinjector comprises a syringe support as described above and a housing, wherein the housing comprises such a syringe support.

In an assembled state, the supporting beam and the flange of the syringe contact one another and are pressed onto one another so that the syringe is securely positioned.

In an exemplary embodiment, the housing comprises an aperture in which the supporting beam is arranged. In particular, the supporting beam is biased radially inwards from the aperture.

In an exemplary embodiment, the housing comprises at least two rigid arms wherein each rigid arm comprises one supporting beam. In particular, the two rigid arms are formed as inner arms which inwardly extend from an outer housing part, e.g. a proximal end, into the housing.

In particular the housing comprises a front part and a rear part wherein the supporting beam is arranged on the rear part. The rear part comprises a proximal end from which the rigid arms are inwardly extended. In this way, the supporting beam is arranged on a distal end of the rear part.

Furthermore, the housing comprises a proximal end which is larger than a proximal aperture of the housing. Thereby, the proximal end of the rear part rests on the edge of the proximal aperture of the front part to proximally close the housing.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitative of the present invention, and wherein.

Corresponding parts are marked with the same reference symbols in all figures.

DETAILED DESCRIPTION

Figure 1:
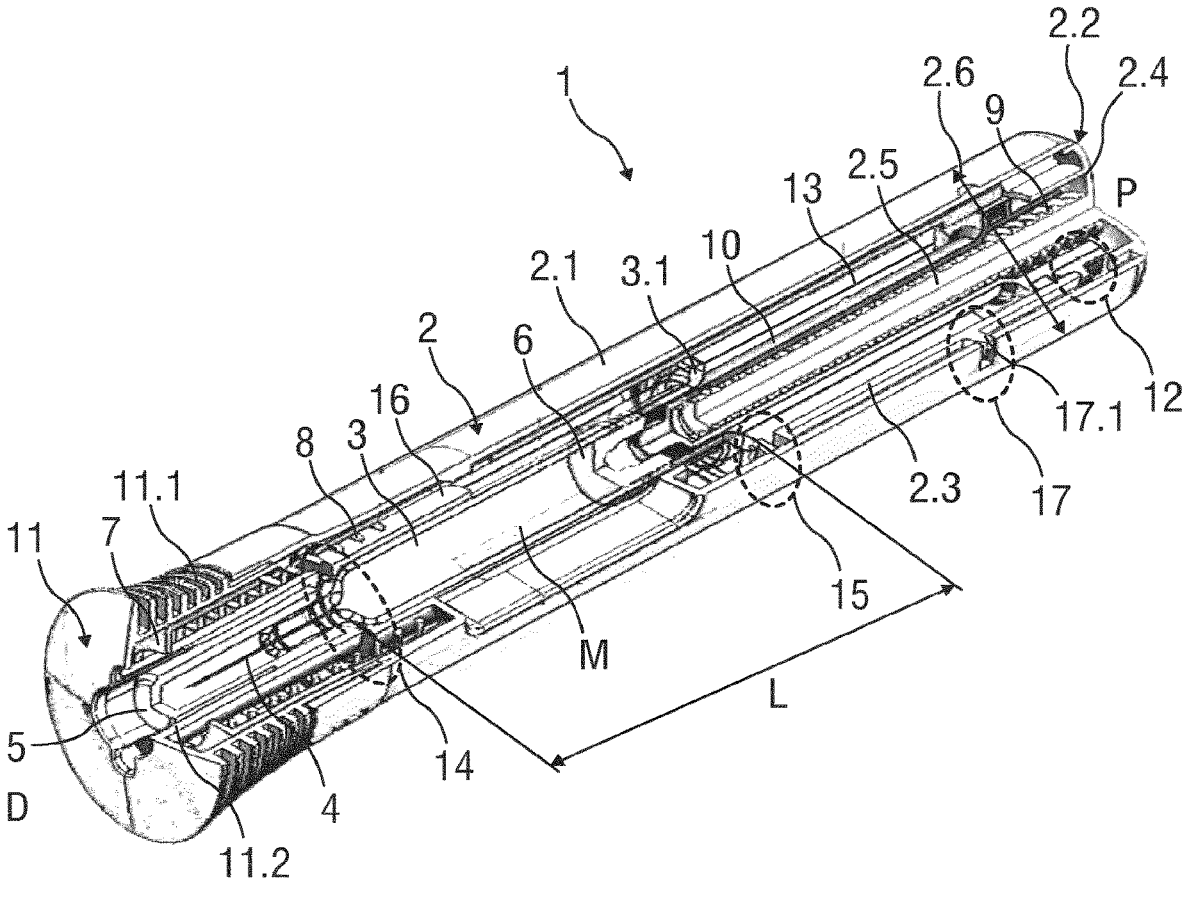
FIG. 1 is a schematic perspective partial section of an exemplary embodiment of an autoinjector.

FIG. 1 is a schematic perspective partial section of an exemplary embodiment of an autoinjector 1 in a state after assembly.

The autoinjector 1 comprises a housing 2 including a sleeve shaped front part 2.1 and a rear part 2.2. Alternatively, the housing 2 may be formed as a one-piece housing (not shown).

The housing 2 is adapted to hold a syringe 3, e.g. a glass syringe. The syringe 3 may be a pre-filled syringe containing a liquid medicament M and have a needle 4 arranged on a distal end. In another exemplary embodiment, the syringe 3 may be a cartridge which includes the medicament M and engages a removable needle (e.g., by threads, snaps, friction, etc.). In the shown exemplary embodiment, the syringe 3 is held in the housing 2 and supported at its proximal end therein by a syringe support 15 further described below.

The autoinjector 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

A stopper 6 is arranged for sealing the syringe 3 in a proximal direction P and for displacing the medicament M contained in the syringe 3 through the needle 4.

The autoinjector 1 further comprises a sleeve shaped needle shroud 7. In an exemplary embodiment, the needle shroud 7 is telescopically coupled to the housing 2 and movable between an extended position relative to the housing 2 in which the needle 4 is covered and a retracted position relative to the housing 2 in which the needle 4 is exposed. Furthermore, a shroud spring 8 is arranged to bias the needle shroud 7 in a distal direction D against the housing 2.

A drive spring 9 in the shape of a compression spring is arranged within a proximal part of the housing 2, in particular the rear part 2.2. A plunger 10 serves for forwarding the force of the drive spring 9 to the stopper 6. In an exemplary embodiment, the plunger 10 is hollow and the drive spring 9 is arranged within the plunger 10, biasing the plunger 10 in the distal direction D against the rear part 2.2. In another exemplary embodiment, the plunger 10 may be solid and the drive 9 may engage a proximal end of the plunger 10. Likewise, the drive spring 9 could be wrapped around the outer diameter of the plunger 10 and extend within the syringe 3.

Furthermore, the autoinjector 1 comprises a cap 11 that may be removably disposed at a distal end of the housing 2, in particular at a distal end of the front part 2.1. The cap 11 may comprise grip features 11.1 for facilitating removal of the cap 11, e.g., by twisting and/or pulling the cap 11 off the case 2. The cap 11 may further include a grip element 11.2, e.g., a barb, a hook, a narrowed section, etc., arranged to engage the protective needle sheath 5, the housing 2 and/or the needle shroud 7. For example, the protective needle sheath 5 is coupled to the cap 11 in a manner that when the cap 11 is removed, the protective needle sheath 5 is also removed from the needle 4.

A plunger release mechanism 12 is arranged for preventing release of the plunger 10 prior to depression of the needle shroud 7 and for releasing the plunger 10 once the needle shroud 7 is sufficiently depressed.

In an exemplary embodiment, the autoinjector 1 further comprises at least one audible indicator 13 for producing an audible feedback for a user or patient indicating that medicament delivery is complete. In other words: The audible indicator 13 is adapted to indicate to a user or a patient that the full dose of medicament M was spent. The audible indicator 13 is formed for example as a bistable spring and is held in the rear part 2.2.

To allow an accurate support of the syringe 3 during and after assembly, the autoinjector 1 comprises a carrier 16 adapted to mount and hold the syringe 3 within the housing 2 in a forward or distal direction D.

A shroud pre-lock mechanism 14 is arranged to prevent depression of the needle shroud 7 when the cap 11 is in place, thus avoiding unintentional activation of the autoinjector 1, e.g. if dropped, during shipping or packaging, etc.

Due to manufacturing tolerance, syringes 3 may have variable lengths L. Thus, a flange 3.1 of the syringe 3 protrudes the carrier 16 in the proximal direction P. To support the axial position of the syringe 3 relative to the housing 2 after assembly, in particular during storage, transportation and normal use, the syringe support 15 comprises one or more supporting beams 15.1 biased radially inwards to accommodate the variable length L of the syringe 3 in an assembled state. The supporting beams 15.1 are adapted to axially bias the syringe 3 in the distal direction D within the housing 2 and to compensate the variable length L of the syringe 3 in the distal direction D. In particular, the syringe support 15 is adapted to accommodate the length L of the syringe 3 of maximum 5% or 3%. For example, the syringe support 15 accommodates +/−1.5 mm of the length L for a syringe 3 of 50 mm in length L.

Figure 2:
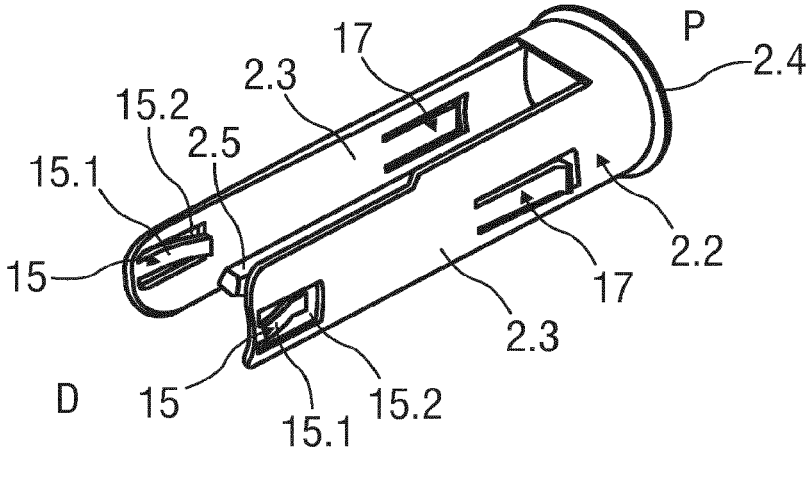
FIG. 2 is a schematic perspective view of an exemplary embodiment of a housing part comprising a syringe support from an inner end.
Figure 3:
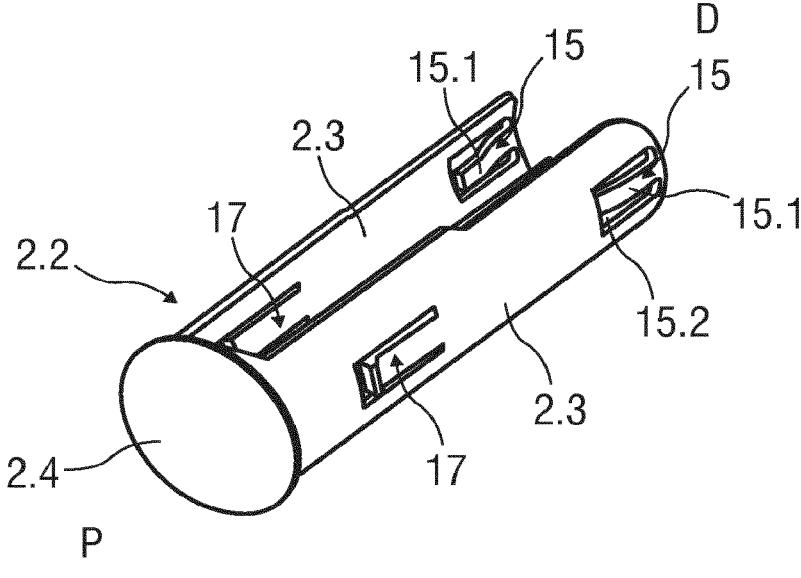
FIG. 3 is a schematic perspective view of an exemplary embodiment of a housing part comprising a syringe support from a proximal end.

FIGS. 2 and 3 are schematic views of the rear part 2.2 of the housing 2. The rear part 2.2 comprises the syringe support 15. The syringe support 15 is adapted to compensate the variable length L of the syringe 3. In detail, the rear part

2.2 comprises at its front or distal end the supporting beams 15.1. The supporting beams 15.1 are formed as resilient arms or flexure beams biased radially inwards to compensate the variable lengths L of the syringe 3.

In the shown embodiment, the rear part 2.2 has a proximal end 2.4. The proximal end 2.4 of the rear part 2.2 is larger than a proximal aperture 2.6 so that the proximal end 2.4 rests on the edge of the proximal aperture 2.6 of the front part 2.1. Two rigid arms 2.3 are extended from the proximal end 2.4 inwards in to the distal direction D.

The shown syringe support 15 comprises two supporting beams 15.1 and a respective number of apertures 15.2 in the rigid arms 2.3. The apertures 15.2 are adapted to receive each of the supporting beams 15.1 when they deflect and stress radially outwards during assembling of the syringe 3 having a variable length L.

The supporting beams 15.1 and the corresponding apertures 15.2 are arranged on a distal end of the rear part 2.2.

The supporting beams 15.1 may be formed from resilient material and in the form of an arc or half-arc.

One end of each supporting beams 15.1 is attached to the aperture 15.2 in the rear part 2.2. The opposite end is a free end. Each supporting beam 15.1 extends radially inwards from the aperture 15.2 so that the supporting beam 15.1 deflects radially outwards into the aperture 15.2 when a syringe 3 with a respective length L is assembled into the syringe carrier 16 and the flange 3.1 of the syringe 3 protrudes the syringe carrier 16 in the proximal direction P. In particular, the supporting beams 15.1 may be integrally moulded with the housing 2, namely with the rear part 2.2.

In an alternative embodiment (not shown), both ends of the supporting beam may be attached to the housing.

Furthermore, the rear part 2.2 comprises a housing lock 17 having a housing lock arm 17.1 to attach the rear part 2.2 onto the front part 2.1. The housing lock arm 17.1 is arranged on a proximal section of the rear part 2.2 and is biased radially outwards.

Figure 4:
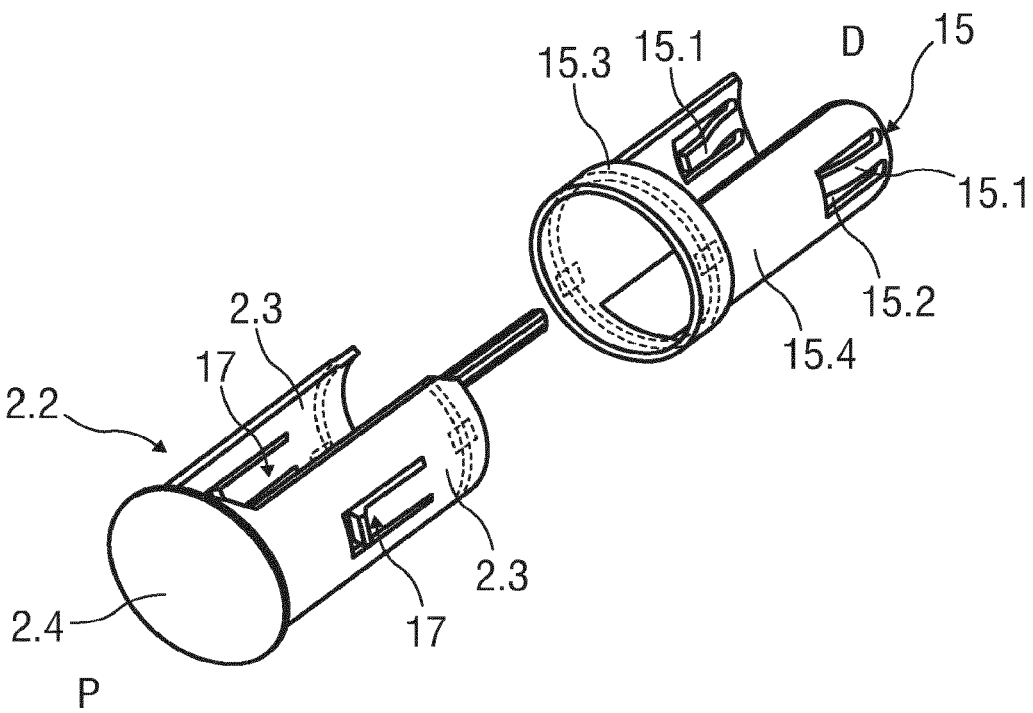
FIG. 4 is a schematic perspective view of an exemplary embodiment of a separate single syringe support and a separate single rear part.

FIG. 4 shows an alternative embodiment of a syringe support 15' formed as a separate single part and the rear part 2.2 formed as a separate single part. The syringe support 15' has a proximal support end 15.3 from which rigid support arms 15.4 comprising the supporting beams 15.1 distally protrude. The proximal support end 15.3 and the housing 2, in particular the front part 2.1 or the rear part 2.2, are correspondingly adapted to retain and hold the syringe support 15' in place on the housing 2, e.g. by securing a rim in a nut or in clips on the housing (shown in dotted line).

The separate rear part 2.2 only comprises the housing lock 17 for releasably connecting the rear part 2.2 with the front part 2.1 to form the housing 2.

Figure 5:
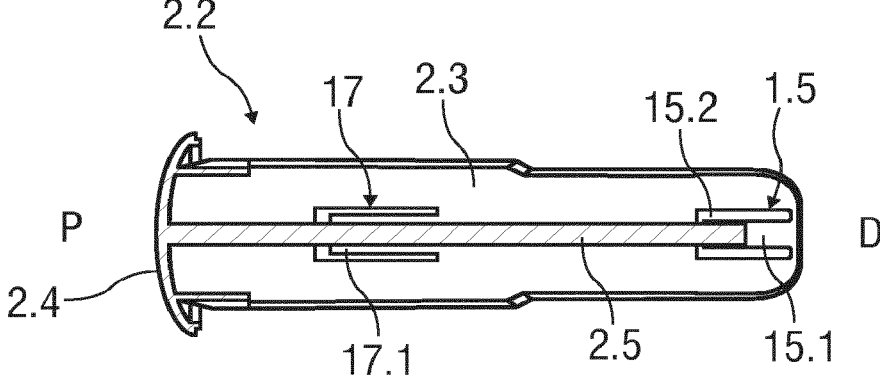
FIG. 5 is a schematic longitudinal section view of an exemplary embodiment of a housing part having a syringe support.

FIG. 5 is a schematic longitudinal section view of the rear part 2.2. The FIG. 5 shows the rear part 2.2 with one supporting beam 15.1 that are part of the syringe support 15. The supporting beam 15.1 is arranged on a distal section of the rear part 2.2 and is biased radially inwards.

The housing lock arms 17.1 attach the rear part 2.2 onto the front part 2.1. The housing lock arms 17.1 are proximally arranged on the rear part 2.2 and are biased radially outwards. The housing lock arms 17.1 retain the rear part 2.2 in position with the front part 2.1.

Figure 6:
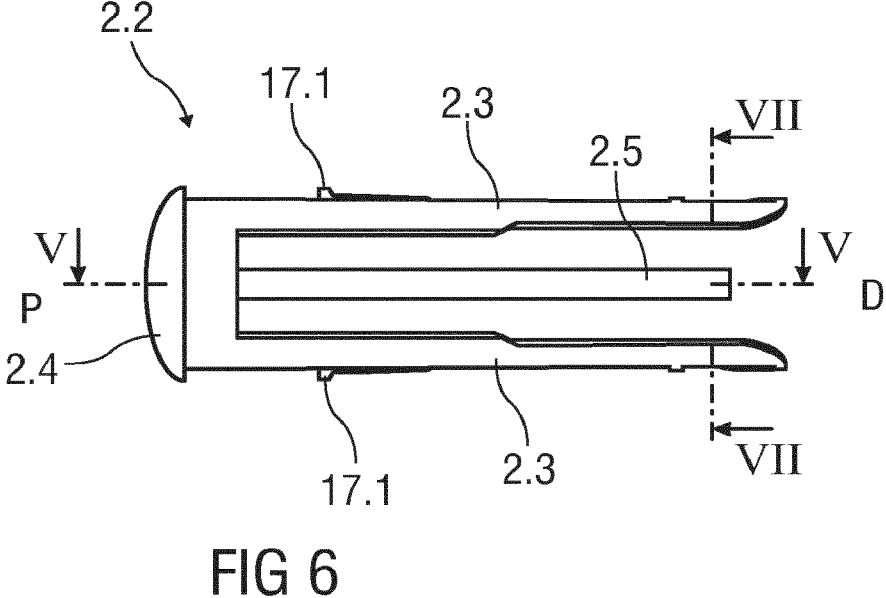
FIG. 6 is a schematic side view of a housing part having a syringe support.

FIG. 6 is a schematic side view of the rear part 2.2 comprising the syringe support 15. To guide the rear part 2.2 during assembling and to support it after assembling and during use, the rear part 2.2 comprises an inner stamp 2.5. The inner stamp 2.5 further supports the assembling and arrangement of the drive spring 9 (see FIG. 1).

Figure 7:
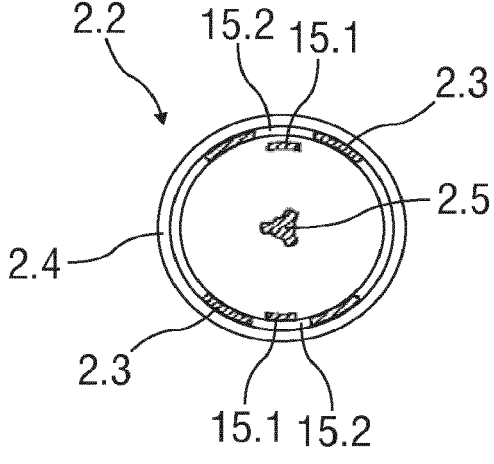
FIG. 7 is a schematic horizontal section view of an exemplary embodiment of a housing part having a syringe support.

FIG. 7 is a schematic horizontal section view of the syringe support 15 according to line VI-VI in FIG. 5. The free ends of the supporting beams 15.1 are biased radially inwards with respect to the rigid arms 2.3.

Figure 8:
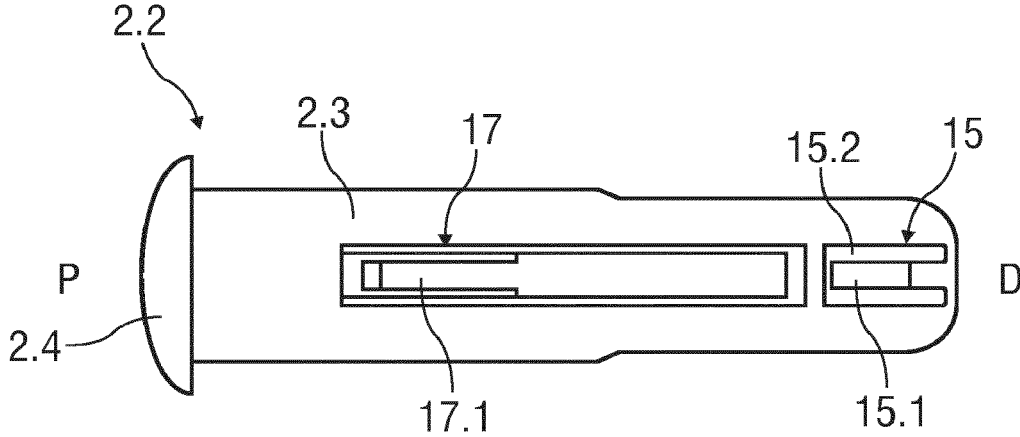
FIG. 8 is a schematic side view of an exemplary embodiment of a housing part having a syringe support.

FIG. 8 is a schematic side view of the rear part 2.2 with the supporting beam 15.1 attached to the aperture 15.2 and arranged on the distal end of the rear part 2.2. The distal end of the supporting beam 15.1 is attached to the aperture 15.2 and the proximal end of the supporting beam 15.1 is formed as a free end biased radially inwards.

FIGS. 9A to 9D are enlarged schematic views of the syringe support 15 formed as part of the rear part 2.2. The syringe support 15 is shown in different positions and in more detail.

Figure 9A:
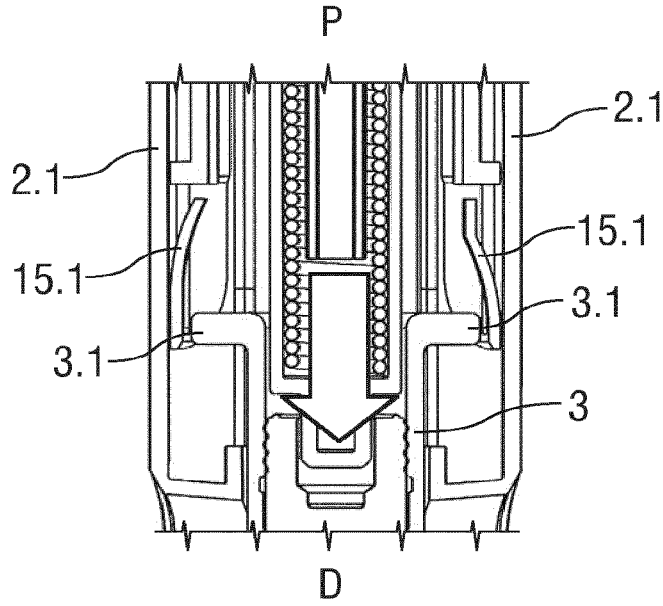
FIGS. 9A to 9D are enlarged schematic views of an exemplary embodiment of a syringe support in different states.

FIG. 9A shows the syringe support 15 while the syringe 3 with a normal length L is in an assembled position.

The at least two supporting beams 15.1 have different free ends wherein one of the free ends is bent and the other free end is straight. The free ends of the arcs of the supporting beams 15.1 are in juxtaposition with the flange 3.1 of the syringe 3.

Furthermore, the different free ends of the supporting beams 15.1 laterally extend beyond a flange 3.1 of the syringe 3. The flange 3.1 abuts the supporting beams 15.1 and the different free ends to provide a secure axial support and positioning of the syringe 3 relative to the housing 2 in the distal direction D. Syringes 3 having variable lengths L may be assembled within the housing 2 wherein the supporting beam 15.1 is deflected radially outwards and stressed so that the variable lengths L of the syringes 3 can be compensated. Hence, a risk of breakage is reduced and manufacturing tolerances may be compensated.

In the shown embodiment, the supporting beams 15.1 are arranged between the flange 3.1 of the syringe 3 and the front part 2.1 of the housing 2.

Figure 9B:
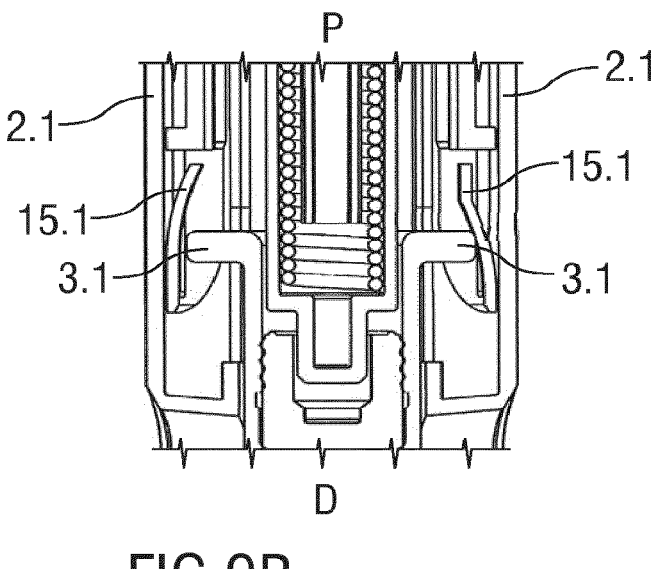
Figure 9C:
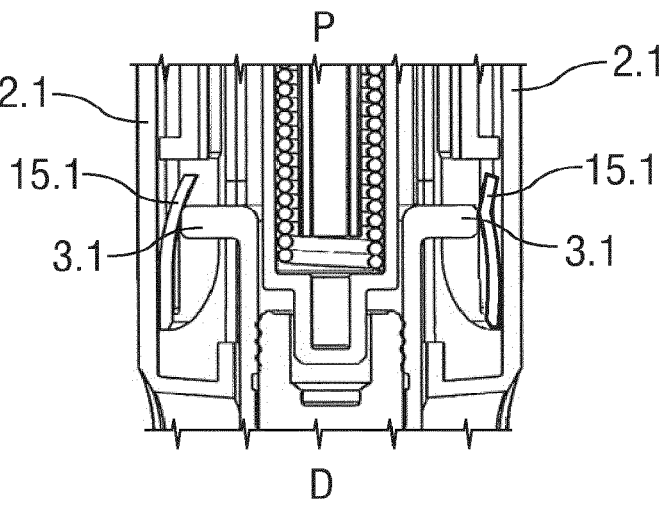
Figure 9D:
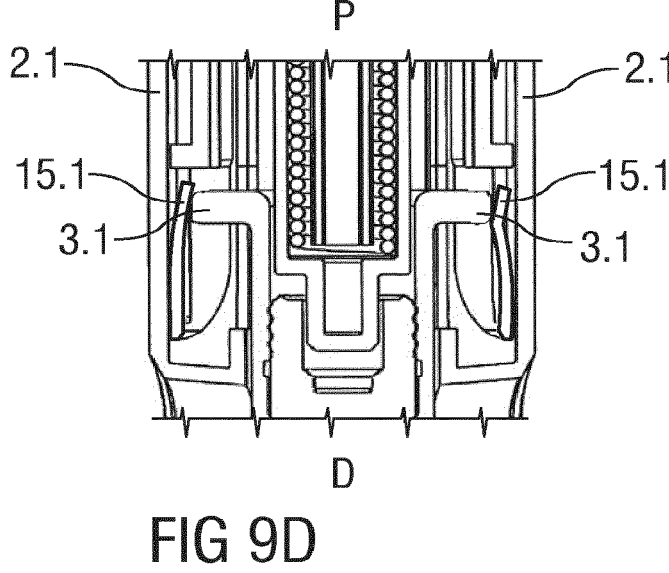

FIGS. 9B to 9D shows further embodiments for the syringe support 15 with assembled syringes 3 of different lengths L. Hence, the syringe support 15 allows compensation of length tolerances of syringes 3 to be assembled.

Figure 10:
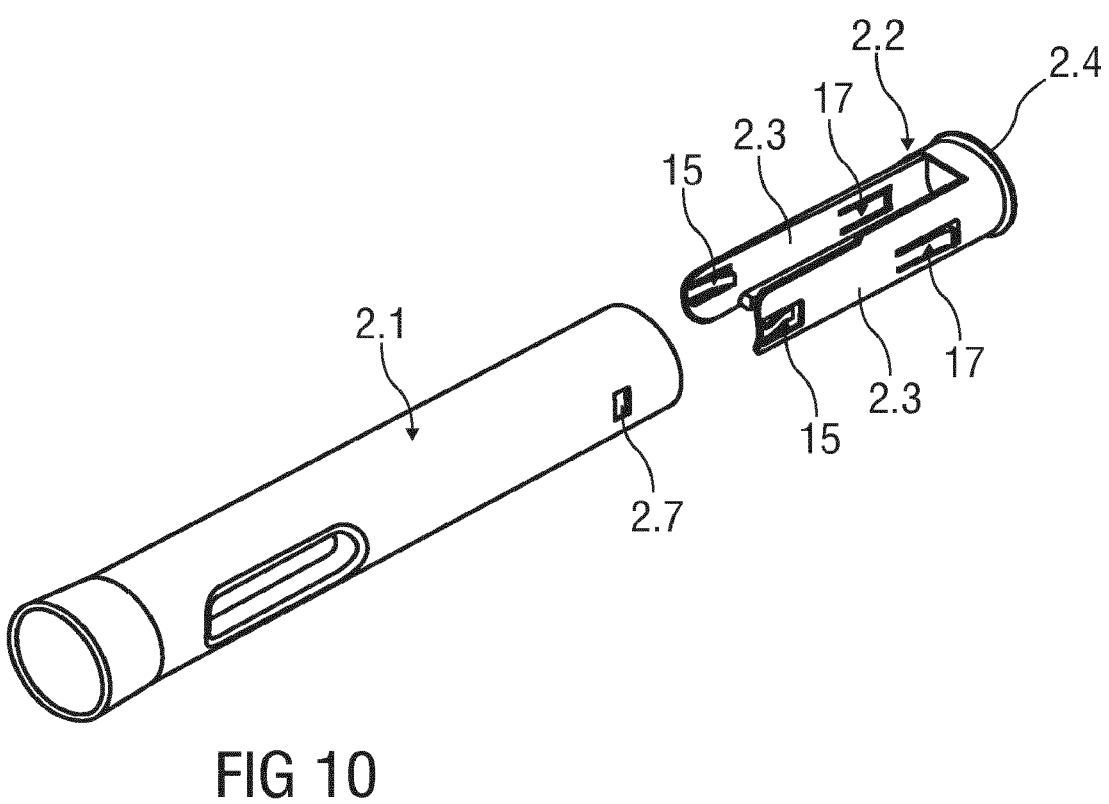
FIG. 10 is an explosion view of a rear part and a front part of a housing.

FIG. 10 shows the front part 2.1 and the rear part 2.2 of the housing. The front part 2.1 and the rear part 2.2 are correspondingly adapted to couple with each other, e.g. by means of a releasable connection formed by e.g. the housing locking arms 17.1 and corresponding slots 2.7.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')₂ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanoates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

LIST OF REFERENCES 1 autoinjector
2 housing
2.1 front part 2.2 rear part
2.3 rigid arm
2.4 proximal end
2.5 stamp
2.6 proximal aperture
2.7 slot
3 syringe
3.1 flange
4 needle
5 protective needle sheath
6 stopper
7 needle shroud
8 shroud spring
9 drive spring
10 plunger
11 cap
11.1 grip feature
11.2 grip element
12 plunger release mechanism
13 audible indicator
14 shroud pre-lock mechanism
15 syringe support
15.1 supporting beam
15.2 aperture
15.3 proximal support end
15.4 rigid support arm
16 carrier
17 housing lock
17.1 housing lock arm
D distal direction
L length
M medicament
P proximal direction

The invention claimed is:

1. An autoinjector comprising: a housing; a drive spring that is arranged within the housing; and a plunger that is adapted to forward a force of the drive spring to a medicament contained in a syringe, wherein the syringe comprises a needle, a flange, and a barrel arranged between the needle and the flange, the autoinjector having a proximal end that is opposite of a distal end of the autoinjector, the distal end of the autoinjector being closer to the needle of the syringe compared to the proximal end of the autoinjector, wherein at least two supporting structures are arranged on the housing, wherein the at least two supporting structures are adapted to bias the flange of the syringe within the housing of the autoinjector, wherein the at least two supporting structures are arranged on the flange, wherein the at least two supporting structures are configured to be stationary relative to the housing after assembly of the autoinjector, wherein a resilient portion of the at least two supporting structures are structure is configured to accommodate variations in length of the barrel, wherein the length of the barrel extends between the needle and the flange, and wherein the at least two supporting structures are configured to securely hold the syringe stationary relative to the housing during insertion of the needle for drug delivery.

2. The autoinjector according to claim 1, wherein the at least two supporting structures are adapted deflect outwardly to exert a radially inwards directed force onto the syringe after assembly of the autoinjector.

3. The autoinjector according to claim 1, wherein the at least two supporting structures are adapted to resiliently deflect to bias the flange of the syringe in a distal direction after assembly of the autoinjector and before activating the autoinjector for injection.

4. The autoinjector according to claim 1, wherein the at least two supporting structures are formed as resilient structures.

5. The autoinjector according to claim 4, wherein the resilient portion of the at least two supporting structures are formed as a bent arc or as a bent half arc in an undeflected position.

6. The autoinjector according to claim 1,
wherein the at least two supporting structures comprise a first supporting structure and a second supporting structure that is arranged opposite to the first supporting structure,
wherein each supporting structure of the at least two supporting structures has a distal end and a proximal end, and
wherein after assembly of the autoinjector, a distance between the first supporting structure and the second supporting structure decreases as viewed by an external viewer when travelling along a longitudinal axis of the autoinjector in a proximal direction.

7. The autoinjector according to claim 6, wherein the distance between the first supporting structure and the second supporting structure decreases along an axial length of the at least two supporting structures as viewed by an external viewer when travelling along the longitudinal axis of the autoinjector in the proximal direction.

8. The autoinjector according to claim 6, wherein the autoinjector comprises at least one rigid body, and
wherein the at least two supporting structures are connected to the at least one rigid body.

9. The autoinjector according to claim 8, wherein the at least two supporting structures are arranged distally on the at least one rigid body.

10. The autoinjector according to claim 8, wherein an inner stamp is arranged within the rigid body,
wherein the inner stamp supports an arrangement of the drive spring,
wherein the drive spring is a compression spring, and
wherein the inner stamp is arranged within the compression spring.

11. The autoinjector according to claim 1, wherein the housing comprises a front part and a rear part, and wherein the at least two supporting structures are arranged on the rear part.

12. The autoinjector according to claim 11, wherein the rear part comprises at least one lock arm arranged on a proximal section of the rear part,
wherein the at least one lock arm is adapted to retain the rear part in position with the front part.

13. The autoinjector according to claim 12, wherein the at least two supporting structures are oriented in a same direction as the at least one lock arm.

14. The autoinjector according to claim 11, wherein a proximal end of the rear part forms a proximal end of the housing of the autoinjector.

15. The autoinjector according to claim 11, wherein the at least two supporting structures are asymmetrical about a longitudinal axis of the autoinjector coaxial with the rear part of the housing.

16. The autoinjector according to claim 1, wherein at least one supporting structure of the at least two supporting structures biases the flange of the syringe in a distal direction.

17. The autoinjector according to claim 1, wherein the at least two supporting structures are configured to be stationary relative to the housing during insertion of the needle and during a time between needle insertion and an end of drug delivery.

18. The autoinjector according to claim 1, comprising the syringe, wherein the syringe comprises a drug.

19. The autoinjector according to claim 1, wherein the at least two supporting structures are adapted to bias the flange of the syringe within the housing of the autoinjector after assembly of the autoinjector.

20. The autoinjector according to claim 1, wherein the at least two supporting structures are configured to be stationary relative to the housing during insertion of the needle.

21. The autoinjector according to claim 1, comprising a needle shroud telescopically coupled to the housing,
   wherein the at least two supporting structures are configured to be stationary relative to the housing during retraction of the needle shroud.

22. A rear part for a housing of an autoinjector and for supporting a position of a syringe relative to a front part of the housing of the autoinjector, the rear part comprising: a distal end, a proximal end that is opposite of the distal end, the distal end of the rear part being closer to a needle of the syringe compared to the proximal end of the rear part, wherein the syringe comprises the needle, a flange, and a barrel arranged between the needle and the flange, wherein the rear part comprises: at least two supporting structures arranged on the rear part, wherein the at least two supporting structures are adapted to bias the flange of the syringe within the housing of the autoinjector, wherein the at least two supporting structures are arranged on the flange, wherein the at least two supporting structures are configured to be stationary relative to the housing after assembly of the autoinjector, and wherein a resilient portion of the at least two supporting structures are configured to accommodate variations in length of the barrel, wherein the length of the barrel extends between the needle and the flange, and wherein the at least two supporting structures are configured to securely hold the syringe stationary relative to the housing during insertion of the needle for drug delivery.

23. The rear part according to claim 22,
   wherein the at least two supporting structures and the flange of the syringe are configured to contact one another and to be pressed onto one another.

24. The rear part according to claim 22, wherein the rear part comprises at least one rigid body,
   and wherein the at least two supporting structures are connected to the rigid body.

25. The rear part according to claim 24, wherein the at least two supporting structures are arranged distally on the rigid body.

26. The rear part according to claim 22, wherein the proximal end is larger than a proximal aperture of the front part of the autoinjector.

27. A method of delivering a drug from an autoinjector, the method comprising: using the autoinjector comprising: a housing, a drive spring that is arranged within the housing, and a plunger that is adapted to forward a force of the drive spring to a medicament contained in a syringe, wherein the syringe comprises a needle, a flange and a barrel arranged between the needle and the flange, wherein the syringe comprises the drug, the autoinjector having a proximal end that is opposite of a distal end of the autoinjector, the distal end of the autoinjector being closer to the needle of the syringe compared to the proximal end of the autoinjector, wherein at least two supporting structures are arranged on the housing, wherein the at least two supporting structures are adapted to bias the flange of the syringe within the housing of the autoinjector, wherein the at least two supporting structures are arranged on the flange, and wherein a resilient portion of the at least two supporting structures are configured to accommodate variations in length of the barrel, wherein the length of the barrel extends between the needle and the flange; holding the at least two supporting structures stationary relative to the housing after assembly of the autoinjector; holding, by the at least two supporting structures, the syringe stationary relative to the housing during insertion of the needle for drug delivery; and moving the plunger relative to the housing to deliver a dose of the drug from the syringe.

\*   \*   \*   \*   \*